(12) United States Patent
Fukutani et al.

(10) Patent No.: US 12,159,418 B2
(45) Date of Patent: Dec. 3, 2024

(54) MEDICAL IMAGE DIAGNOSTIC APPARATUS AND MARKER

(71) Applicants: CANON KABUSHIKI KAISHA, Tokyo (JP); CANON MEDICAL SYSTEMS CORPORATION, Tochigi (JP)

(72) Inventors: Kazuhiko Fukutani, Kanagawa (JP); Toru Sasaki, Kanagawa (JP); Ryuichi Nanaumi, Tokyo (JP)

(73) Assignees: Canon Kabushiki Kaisha, Tokyo (JP); Canon Medical Systems Corporation, Tokyo (JP)

( * ) Notice: Subject to any disclaimer, the term of this patent is extended or adjusted under 35 U.S.C. 154(b) by 595 days.

(21) Appl. No.: 17/354,383

(22) Filed: Jun. 22, 2021

(65) Prior Publication Data

US 2021/0407106 A1    Dec. 30, 2021

(30) Foreign Application Priority Data

Jun. 24, 2020    (JP) .............................. 2020-109120

(51) Int. Cl.
*G06T 7/246*    (2017.01)
*A61B 5/055*    (2006.01)
*A61B 90/00*    (2016.01)
*G03H 1/00*    (2006.01)

(52) U.S. Cl.
CPC .............. *G06T 7/246* (2017.01); *A61B 5/055* (2013.01); *A61B 90/39* (2016.02); *G03H 1/0005* (2013.01); *A61B 2090/3937* (2016.02); *G03H 2001/0033* (2013.01); *G06T 2207/10088* (2013.01); *G06T 2207/30004* (2013.01); *G06T 2207/30204* (2013.01)

(58) Field of Classification Search
CPC ....... G06T 7/0012; G06T 7/246; G06T 7/248; G06T 7/70; G06T 7/73; G06T 7/74; G06T 2207/30204; G06T 2207/30208; A61B 5/1127; A61B 5/1128; A61B 6/0492; A61B 90/39; A61B 2090/3937; A61B 2090/3983

See application file for complete search history.

(56) References Cited

U.S. PATENT DOCUMENTS

| | | |
|---|---|---|
| 8,121,361 B2 | 2/2012 | Ernst et al. |
| 8,848,977 B2 | 9/2014 | Bammer et al. |
| 2015/0168136 A1* | 6/2015 | Kamat et al. ........... E02F 9/264 348/136 |
| 2016/0035108 A1* | 2/2016 | Yu et al. ................ A61B 5/721 382/131 |
| 2017/0360401 A1* | 12/2017 | Rothberg et al. .... G06V 30/194 |
| 2021/0137634 A1* | 5/2021 | Lang ..................... A61B 5/113 |

\* cited by examiner

*Primary Examiner* — Andrew W Johns
(74) *Attorney, Agent, or Firm* — Canon U.S.A., Inc., IP Division

(57) ABSTRACT

A medical image diagnostic apparatus includes a marker to be placed on a subject, at least one imaging unit configured to capture images of the subject and the marker, and a detection unit configured to detect movement of the marker from the images captured by the imaging unit. The marker includes a plurality of planar structures that can be detected by the detection unit, and the planar structures are spaced apart from each other with a distance no less than a predetermined distance.

11 Claims, 12 Drawing Sheets

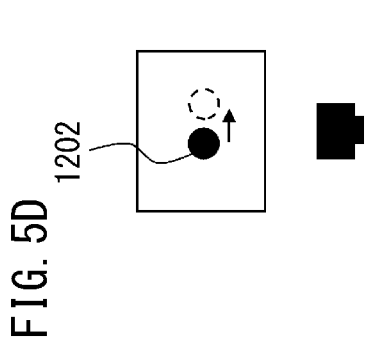 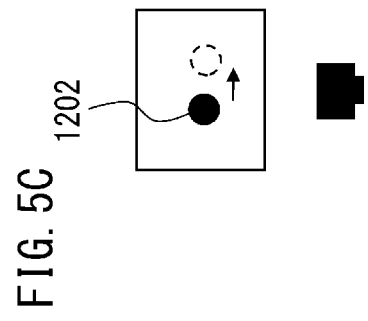 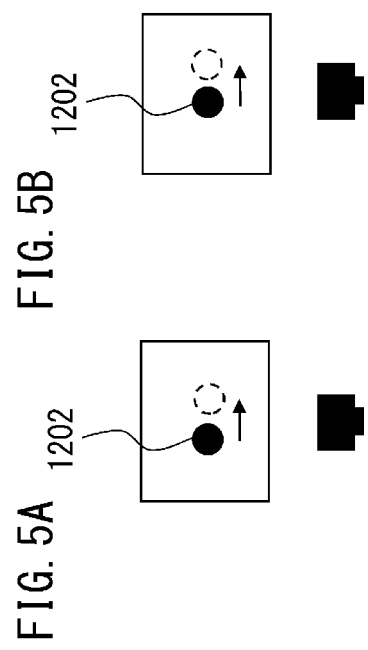
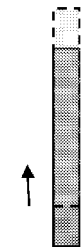 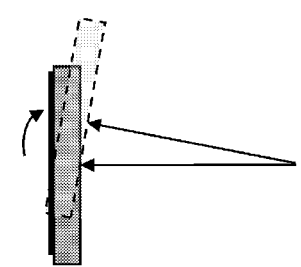 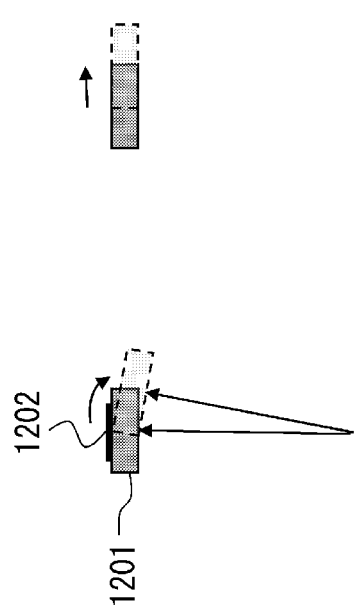
FIG. 5A  FIG. 5B  FIG. 5C  FIG. 5D FIG. 6A
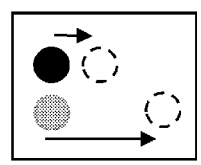
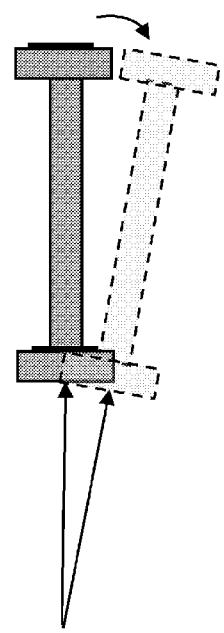
FIG. 6B
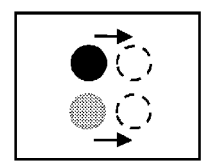
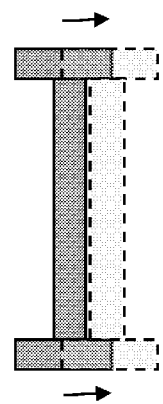

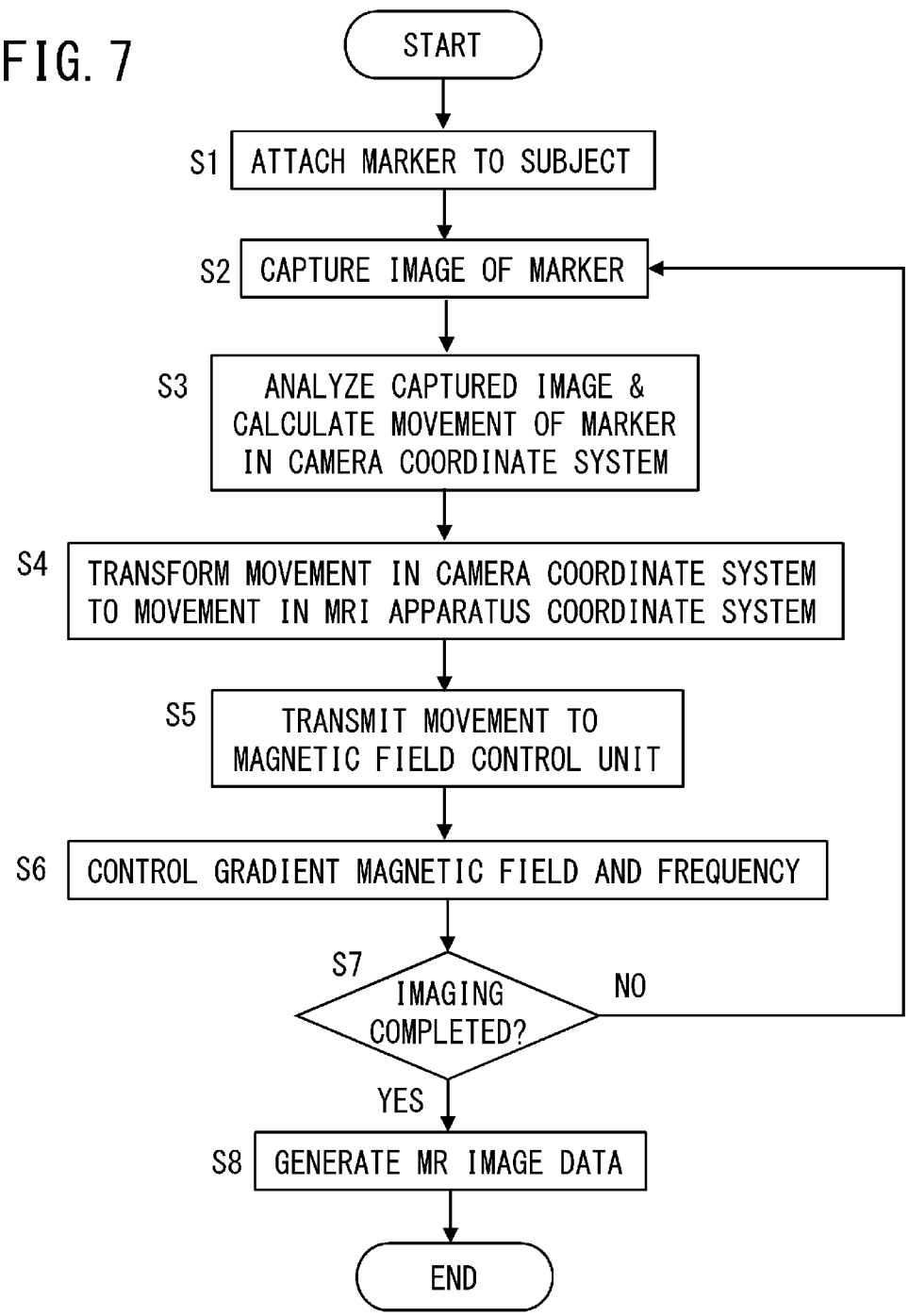

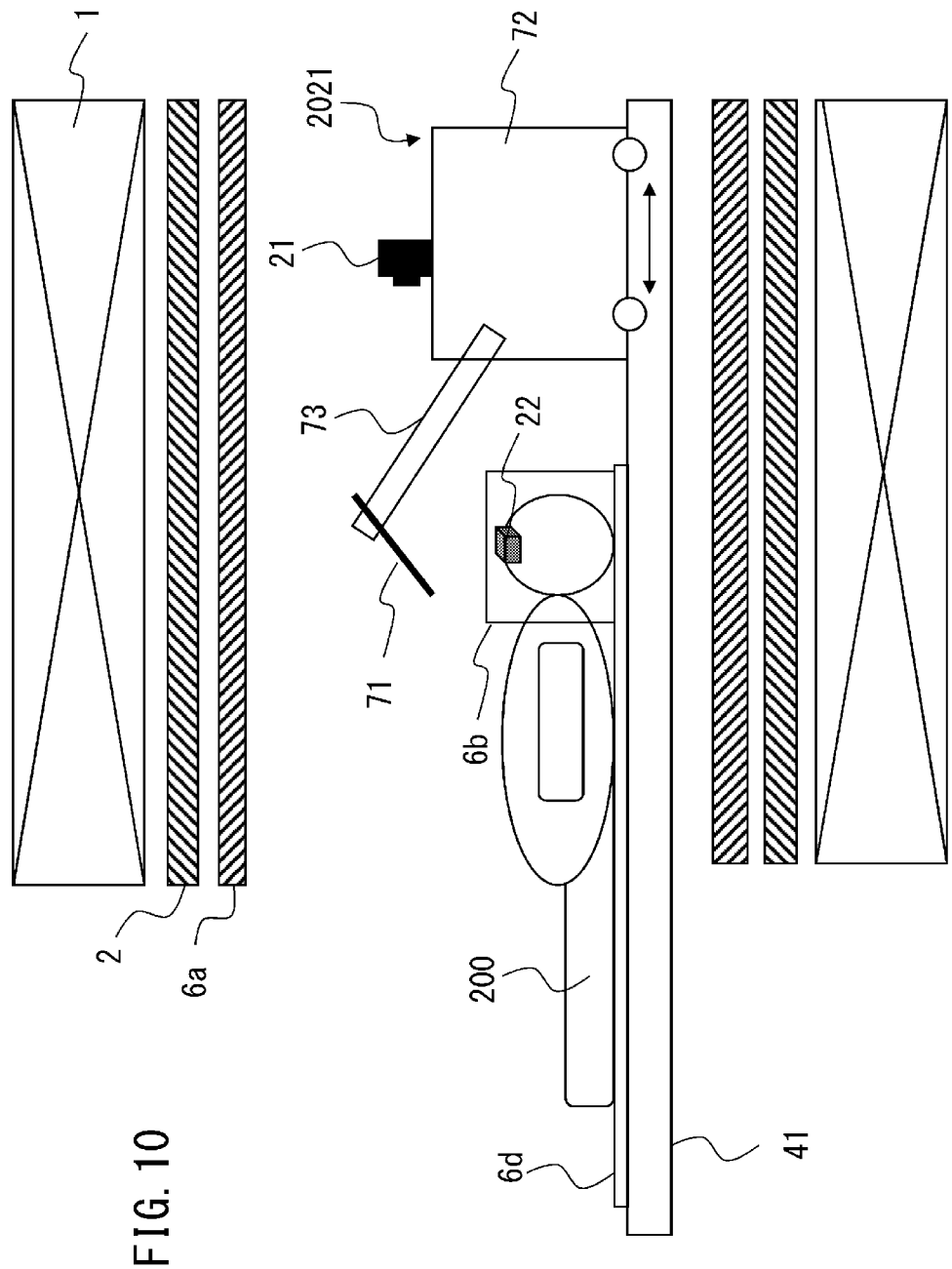

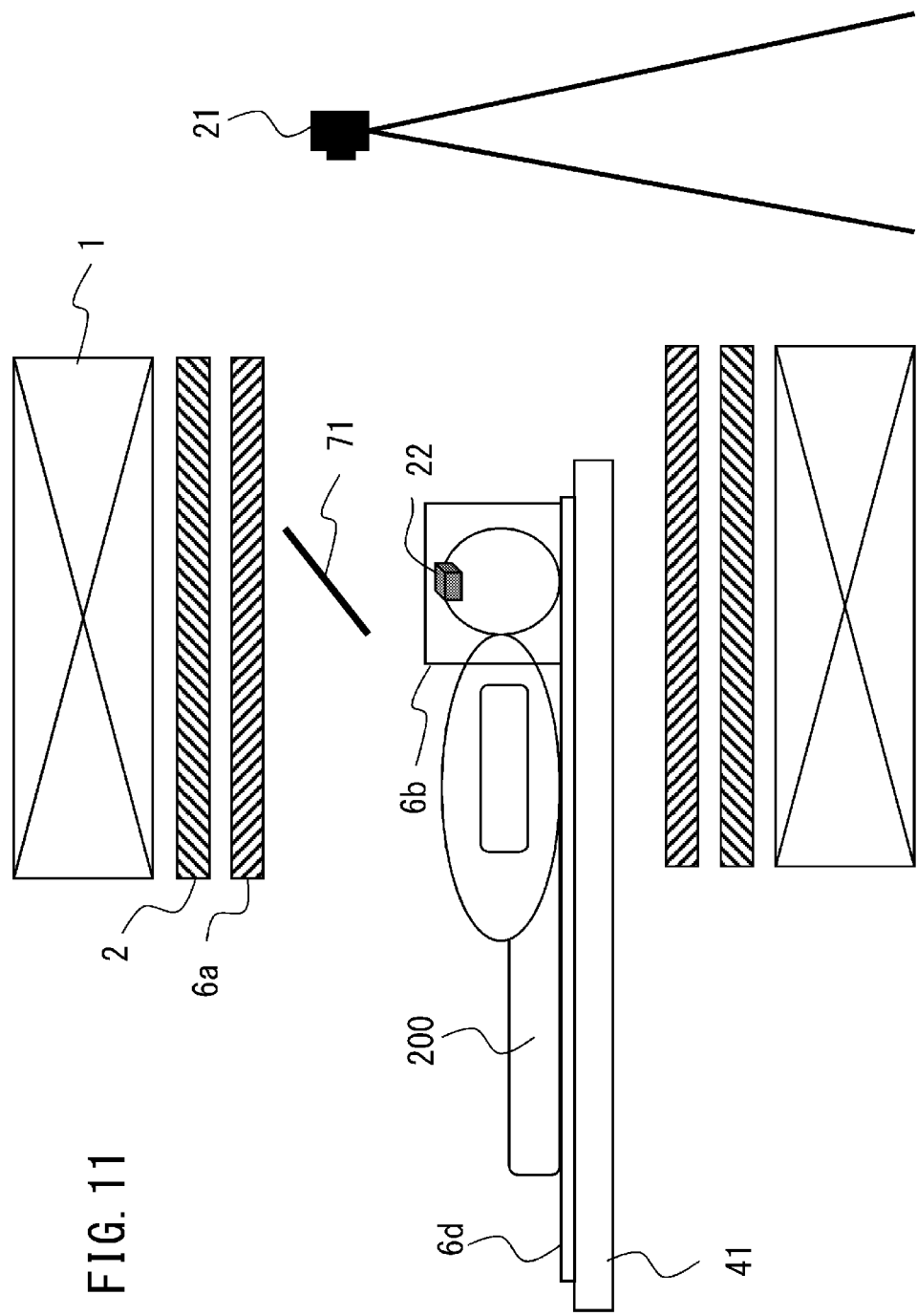

MEDICAL IMAGE DIAGNOSTIC APPARATUS AND MARKER

BACKGROUND

Field of the Disclosure

The present disclosure relates to a medical image diagnostic apparatus, and a marker for detecting motion artifacts in an image.

Description of the Related Art

As medical image diagnostic apparatuses that image subjects, not only a magnetic resonance imaging (MRI) apparatus but also various modalities are used.

For example, the MRI apparatus applies a radio frequency (RF) magnetic field to a subject placed in a static magnetic field and generates, based on a magnetic resonance (MR) signal generated from the subject, an image of an inside of the subject.

In such a modality, when the subject moves while being imaged, so-called motion artifacts may occur in an image and, in this case, the subject is to be imaged again, resulting in an increased load on the subject.

A specification of U.S. Pat. No. 8,121,361 discloses, as a technique of preventing occurrence of the motion artifacts, tracking a marker having a moire pattern fixed to a subject by using a camera image, and feedbacking information on movement of the marker to an MRI apparatus, and thereby controlling scanning.

Meanwhile, a specification of U.S. Pat. No. 8,848,977 discloses a technique of fixing to a subject a large marker, relative to an imaging range of a camera and causing a portion of an identifiable pattern attached to the marker to be inevitably included in a viewing field of the camera during imaging.

SUMMARY

According to an aspect of the present disclosure, it is provided a medical image diagnostic apparatus including a marker to be placed on a subject, at least one imaging unit configured to capture images the subject and the marker, and a detection unit configured to detect movement of the marker from an image that is imaged by the imaging unit. The marker includes a plurality of planar structures that can be detected by the detection unit, and the planar structures are disposed to be spaced apart from each other with a distance no less than a predetermined distance. In addition, according to an aspect of the present disclosure, it is provided a medical image diagnostic apparatus including a marker to be placed on a subject, at least one imaging unit configured to capture images the subject and the marker, and a detection unit configured to detect movement of the marker from an image that is imaged by the imaging unit. The marker includes a structure having a three-dimensional shape and formed of a plurality of planes each being provided with a pattern having a plurality of feature points to allow the detection unit to detect the movement of the marker. Further, according to an aspect of the present disclosure, it is provided a medical image diagnostic apparatus including a marker to be placed on a subject, at least one imaging unit that images the subject and the marker, and a detection unit that detects movement of the marker from an image that is imaged by the imaging unit. The marker has a pattern formed by hologram.

According to an aspect of the present disclosure, it is provided a marker for detecting movement of a subject, including a plurality of planar structures that can be detected by a medical image diagnostic apparatus. The marker is placed on the subject and images of the marker are captured together with the subject by the medical image diagnostic apparatus so as to reduce a motion artifact in the images captured by the medical image diagnostic apparatus, and the planar structures are spaced apart from each other by a distance not less than a predetermined distance. In addition, according to an aspect of the present disclosure, it is provided a marker for detecting movement of a subject, including a structure having a three-dimensional shape and formed of a plurality of planes each being provided with a pattern having a plurality of feature points that allow a medical image diagnostic apparatus to detect movement of the marker. The marker is placed on the subject and images of the marker are captured together with the subject by the medical image diagnostic apparatus so as to reduce a motion artifact in the images captured by the medical image diagnostic apparatus. Further, according to an aspect of the present disclosure, it is provided a marker for detecting movement of a subject, including a pattern formed by hologram. The marker is placed on the subject and images of the marker are captured together with the subject by a medical image diagnostic apparatus so as to reduce a motion artifact in the images captured by the medical image diagnostic apparatus, and the marker.

Further features of the present invention will become apparent from the following description of exemplary embodiments with reference to the attached drawings.

BRIEF DESCRIPTION OF THE DRAWINGS

FIGS. 5A to 5D are diagrams illustrating an example of an effect of a marker according to a conventional example;

FIGS. 6A and 6B are diagrams illustrating an example of an effect of the marker according to the first embodiment;

FIG. 7 is a flow chart illustrating an example of a processing procedure according to the first embodiment;

FIG. 10 is a diagram illustrating an example of a configuration of a magnetic resonance imaging apparatus according to another modification;

FIG. 11 is a diagram illustrating an example of a configuration of a magnetic resonance imaging apparatus according to still another modification.

DESCRIPTION OF THE EMBODIMENTS

Figure 1:
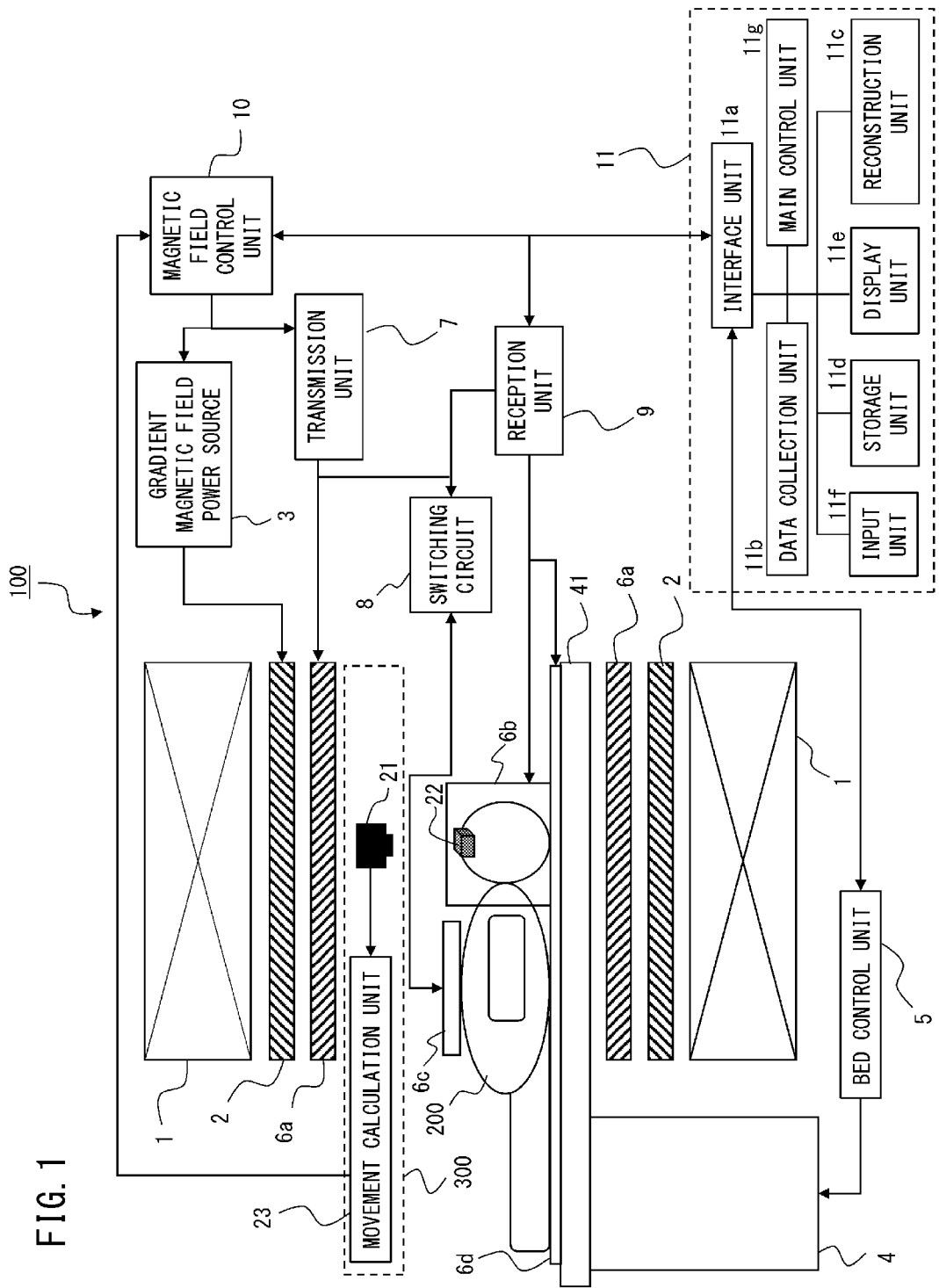
FIG. 1 is a diagram illustrating a configuration of a magnetic resonance imaging apparatus according to a first embodiment.

In the related art technique described above, when the imaging range of the camera is not changed and a size of the marker is reduced, detection accuracy of the movement of the marker may deteriorate.

Therefore, in view of the foregoing, the present disclosure provides a technique which can prevent deterioration of detection accuracy of movement of a marker to be used during imaging of a subject.

Referring to the drawing, embodiments of the present disclosure will be described below. It is assumed that the same or equivalent components, members, and processing illustrated in individual drawings are given the same reference numerals, and a repeated description thereof is omitted appropriately. In addition, in each of the drawings, some of the components, the members, and the processing are omitted.

Referring to the drawings, a detailed description will be given below of an embodiment of a medical image diagnostic apparatus of the present disclosure. Note that, as the medical image diagnostic apparatus, any modality capable of imaging a subject can be used. Specifically, a medical image diagnostic apparatus 10 according to the present embodiment is applicable to a single modality such as an MRI apparatus or an X-ray computed tomography (CT) apparatus. The medical image diagnostic apparatus 10 is also applicable to a single modality such as a positron emission tomography (PET) apparatus. The medical image diagnostic apparatus 10 is also applicable to a single modality such as a single photon emission computed tomography (SPECT) apparatus. Alternatively, the medical image diagnostic apparatus according to the present embodiment may also be applied to a composite modality such as an MR/PET apparatus, a CT/PET apparatus, an MR/SPECT apparatus, or a CT/SPECT apparatus. Note that, in a specific example in the following description, the medical image diagnostic apparatus 10 according to the present embodiment is assumed to be a magnetic resonance imaging apparatus. However, the following description is applicable to the various modalities mentioned above.

First Embodiment

FIG. 1 is a diagram illustrating a configuration of a magnetic resonance imaging apparatus 100 serving as a medical image diagnostic apparatus according to the first embodiment. The magnetic resonance imaging apparatus 100 includes a static magnetic field magnet 1, a gradient magnetic field coil 2, a gradient magnetic field power source 3, a bed 4, a bed control unit 5, RF coil units 6a, 6b, 6c, and 6d, a transmission unit 7, a switching circuit 8, and a reception unit 9. The magnetic resonance imaging apparatus 100 also includes a magnetic field control unit 10, a calculator system 11, an optical imaging unit 21, a marker 22, and a movement calculation unit 23.

The static magnetic field magnet 1 is a magnet having a hollow cylindrical shape and generates a uniform static magnetic field in an inner space of the magnetic resonance imaging apparatus 100. Examples of the static magnetic field magnet 1 include a superconducting magnet.

The gradient magnetic field coil 2 is a coil having a hollow cylindrical shape and disposed inside the static magnetic field magnet 1. The gradient magnetic field coil 2 is formed of a combination of three coils of different types corresponding respectively to an X-axis, a Y-axis, and a Z-axis which are perpendicular to each other. In the gradient magnetic field coil 2, the three coils mentioned above receive individual current supplies from the gradient magnetic field power source 3 to generate gradient magnetic fields in which magnetic field intensities have respective gradients along the X-axis, the Y-axis, and the Z-axis. Note that a Z-axis direction is assumed to be the same as, e.g., a static magnetic field direction. The individual gradient magnetic fields along the X-axis, the Y-axis, and the Z-axis correspond to, e.g., a slice-selection gradient magnetic field Gs, a phase-encoding gradient magnetic field Ge, and a readout gradient magnetic field Gr, respectively. The slice-selection gradient magnetic field Gs is used so as to optionally determine an imaging cross section. The phase-encoding gradient magnetic field Ge is used so as to change a phase of a magnetic resonance signal depending on a spatial position. The readout gradient magnetic field Gr is used so as to change a frequency of the magnetic resonance signal depending on the spatial position.

A subject 200 is moved into an inner space (imaging space) of the gradient magnetic field coil 2, while being placed on a top plate 41 of the bed 4. Note that this imaging space is referred to as a bore. The bed 4 moves the top plate 41 in a longitudinal direction thereof (left-right direction in FIG. 1) and a vertical direction under the control of the bed control unit 5. In general, the bed 4 is disposed such that the longitudinal direction is parallel with a direction in which a center axis of the static magnetic field magnet 1 extends.

The RF coil unit 6a is a coil unit for transmitting an RF signal. The RF coil unit 6a is formed by causing one or a plurality of coils to be contained in a case having a cylindrical shape. The RF coil unit 6a is disposed inside the gradient magnetic field coil 2. The RF coil unit 6a receives a supply of the radio frequency signal (RF signal) from the transmission unit 7 to generate a radio frequency magnetic field (RF magnetic field). The RF coil unit 6a generates the RF magnetic field in a region including a major part of the subject 200. In other words, it can be said that the RF coil unit 6a includes a so-called whole body (WB) coil.

The RF coil units 6b and 6d are coil units for receiving the radio frequency signal. The RF coil units 6b and 6d are placed on the top plate 41, embedded in the top plate 41, or attached to the subject 200. As illustrated in the drawing, it may also be possible that the subject 200 is placed on the RF coil unit 6d. When the subject 200 is to be imaged, the RF coil units 6b and 6d are moved together with the subject 200 into the bore. The RF coil units 6b and 6d can be selected appropriately from among coil units of various types. The RF coil units 6b and 6d detect a magnetic resonance signal generated in the subject 200. In particular, the RF coil unit 6b of a type to be attached to a head region of the subject 200 is referred to as the head RF coil 6b.

The RF coil unit 6c is a coil unit for transmitting/receiving the radio frequency signal. Note that the RF coil unit 6c may also be such that a coil unit for transmitting the radio frequency signal and a coil unit for receiving the radio frequency signal are separately configured. The RF coil unit 6c is placed on the top plate 41, embedded in the top plate 41, or attached to the subject 200. When the subject 200 is to be imaged, the RF coil unit 6c is moved together with the subject 200 into the bore. The RF coil unit 6c can be selected appropriately from among coil units of various types. The RF coil unit 6c receives a supply of the RF signal from the transmission unit 7 to generate the RF magnetic field. The RF coil unit 6c also detects the magnetic resonance signal generated in the subject 200. As the RF coil unit 6c, an array coil in which a plurality of coil elements are arranged can be used. The RF coil unit 6c generates the RF magnetic field smaller in size than that generated by the RF coil unit 6a and including only a local area of the subject 200. In other words, it can be said that the RF coil unit 6c includes a local coil. Note that, as the head RF coil, a local coil for transmitting/receiving the RF signal may also be used.

The transmission unit 7 selectively supplies an RF pulse corresponding to a Lamor frequency to the RF coil unit 6a or to the RF coil unit 6c. Note that the transmission unit 7 supplies respective RF pulses having different amplitudes and different phases to the RF coil unit 6a and to the RF coil unit 6c depending on a size difference between the respective RF magnetic fields to be formed thereby or the like. The switching circuit 8 connects the RF coil unit 6c to the transmission unit 7 during a transmission period during which the RF magnetic field is to be generated, while connecting the RF coil unit 6c to the reception unit 9 during a reception period during which the magnetic resonance signal is to be detected. Note that the calculator system 11 notifies the transmission unit 7 of the transmission period and the reception period.

The reception unit 9 performs processing such as amplification, phase detection, or analog-digital conversion on the magnetic resonance signal detected by each of the RF coil units 6b and 6c to obtain magnetic resonance data. The calculator system 11 includes an interface unit 11a, a data collection unit 11b, a reconstruction unit 11c, a storage unit 11d, a display unit 11e, an input unit 11f, and a main control unit 11g.

The interface unit 11a is connected to each of the magnetic field control unit 10, the bed control unit 5, the transmission unit 7, the switching circuit 8, and the reception unit 9. The interface unit 11a inputs/output signals transmitted/received between the individual units connected thereto and the calculator system 11.

The data collection unit 11b collects the magnetic resonance data output from the reception unit 9. The data collection unit 11b stores the collected magnetic resonance data in the storage unit 11d.

The reconstruction unit 11c performs post-processing, i.e., reconstruction processing such as Fourier transform on the magnetic resonance data stored in the storage unit 11d to generate spectrum data or MR image data of intended nuclear spin in the subject 200.

The storage unit 11d stores the magnetic resonance data and the spectrum data or the image data for each of the subjects.

The display unit 11e displays various data such as the spectrum data and the image data under the control of the main control unit 11g. As the display unit 11e, a display device such as a liquid crystal display can be used.

The input unit 11f receives various instructions and information each input thereto from an operator. As the input unit 11f, a pointing device such as a mouse or a trackball, a selection device such as a mode changeover switch, or an input device such as a keyboard can be used appropriately.

The main control unit 11g includes a CPU, a memory, and the like each not shown and controls an overall operation of the magnetic resonance imaging apparatus 100.

The magnetic field control unit 10 varies each of the gradient magnetic fields in accordance with a required pulse sequence under the control of the main control unit 11g and also controls the gradient magnetic field power source 3 and the transmission unit 7 to transmit an RF pulse at a predetermined frequency. In addition, the magnetic field control unit 10 varies the gradient magnetic fields and frequencies based on information on movement of the subject 200 transmitted from the movement calculation unit 23. Note that the function of the magnetic field control unit 10 may also be integrated as one of the functions of the main control unit 11g. While the gradient magnetic fields and the frequencies are varied herein, either one of the gradient magnetic fields and the frequencies may also be varied.

The optical imaging unit 21 images, together with the subject 200, the marker 22 for detecting the movement of the subject, which is intended to reduce motion artifacts, and the movement calculation unit 23 detects the movement of the marker 22 from an image captured by the optical imaging unit 21. The movement calculation unit 23 corresponds to a detection unit that detects the movement of the marker from the image captured by the imaging unit. The movement detection unit 23 transmits movement information representing the detected movement of the marker 22 to the magnetic field control unit 10. The magnetic field control unit 10 controls the gradient magnetic fields and the frequencies based on the received movement information to hold an imaging area of the subject 200 substantially constant. This allows image data in which motion artifacts are prevented from being formed to be obtained even when the subject 200 moves. In other words, the magnetic resonance imaging apparatus 100 allows the image data in which the movement of the subject 200 is corrected to be obtained. Note that it may also be possible to control an operation of an optionally selected functional unit in the apparatus other than the magnetic field control unit 10 based on the movement of the marker 22 detected by the movement detection unit 23.

When the "movement" mentioned herein is movement of a rigid body in a three-dimensional space, the "movement" generally indicates six-degree-of-freedom movement, which is movement represented by three axes of rotation and three axes of translation. In the present specification also, the six-degree-of-freedom movement is described by way of example, but a degree of movement of any number may be used appropriately as long as the degree of movement can represent the movement of the subject 200.

The optical imaging unit 21 is typically an optical camera, but any imaging apparatus may be used appropriately as long as the imaging apparatus can image or capture the movement of the marker 22. When the optical imaging unit 21 is the optical camera, the optical imaging unit 21 is formed of at least one or more optical cameras, and preferably two or more optical cameras. As the number of the optical cameras of the optical imaging unit 21 increases, measurement accuracy of movement of the subject 200 along various axes increases.

Preferably, the optical imaging unit 21 is MR-compatible. The wording "MR-compatible" mentioned herein means that a configuration which reduces noise that affects image data during MR imaging is used and, even in a strong magnetic field environment, a normal operation is performed. Examples of the MR-compatible optical imaging unit 21 include a magnetically shielded camera using a non-magnetic material.

In addition, as illustrated in FIG. 1, the optical imaging unit 21 is preferably disposed in the bore which is a space surrounded by the static magnetic field magnet 1 and the gradient magnetic field coil 2. This allows the marker 22 to be imaged at a place closer to the marker 22. In other words, in the optical imaging unit 21, a lens configuration need not be complicated to image the marker 22. Note that, when the optical imaging unit 21 cannot be disposed inside the bore, a movement imaging unit may also be disposed outside the bore. In this case, when the optical imaging unit 21 is a camera, it is required to use a lens having a long focal distance or the like and image the marker 22 in a relatively large size. Alternatively, it may also be possible to use a camera serving as the optical imaging unit 21 and directly image the marker or use a mirror or the like as a reflective member and image the marker. In other words, as long as the marker 22 can be imaged in a predetermined size (imaging size), the optical imaging unit 21 can be disposed at any position in the magnetic resonance imaging apparatus 100.

An imaging range of the optical imaging unit 21 corresponds to a range in which the entire marker 22 can be imaged described later. For example, when a minimum virtual cube completely including the marker 22 is assumed, the imaging range of the optical imaging unit 21 needs to be larger than a maximum cross-sectional area of the virtual cube. In other words, a size of the marker 22 needs to be included in the imaging range of the optical imaging unit 21. For example, when the imaging range of the optical imaging unit 21 is given by 60×40 mm, the maximum cross-sectional area of the minimum cube surrounding the entire marker 22 is not more than 60×40 mm Note that, when the optical imaging unit 21 is a camera, the imaging range of the optical imaging unit 21 is determined by a size of an image sensor, a focal distance of a lens, and a distance from an optical center of the camera to the subject (which is the marker 22 herein). Note that it may also be possible to determine the imaging range of the optical imaging unit 21 including also a range in which the marker 22 moves during imaging.

Note that, when the optical imaging unit 21 is a camera, an illumination unit (nor shown) that illuminates the marker 22 with light may also be used. By using the illumination unit, the optical imaging unit 21 can image the marker 22 or feature points or patterns formed on the marker 22 with a high contrast. The illumination unit is also preferably MR-compatible, and an MR-compatible LED illumination device, an MR-compatible fiber illumination device, or the like can be used. As the light emitted from the illumination unit for the illumination, light at any wavelength or in any wavelength band may be used as long as the light allows the marker 22 or the patterns formed on the marker 22 to be imaged with a high contrast.

The movement calculation unit 23 analyzes an image captured by the optical imaging unit 21 and calculates the movement of the marker 22 or the movement of the subject 200. For example, the movement calculation unit 23 has, as hardware resources, a processor such as a CPU, a GPU, or an MPU and a memory such as a ROM or a RAM. Note that an application specific integrated circuit (ASIC) may be used for the movement calculation unit 23. Alternatively, a field programmable logic device (FPGA) may also be used for the movement calculation unit 23. The movement calculation unit 23 may also be implemented by another complex programmable logic device (CPLD). Alternatively, the movement calculation unit 23 may also be implemented by a simple programmable logic device (SPLD). Note that the optical imaging unit 21 and the movement calculation unit 23 that calculate the movement of the subject 200 by using the marker 22 are collectively referred to as a movement measurement system 300. Note that, in general, the movement calculation unit 23 is disposed outside the bore, particularly outside a test chamber to be prevented from affecting MR imaging. However, as long as the movement calculation unit 23 does not affect the MR imaging, the movement calculation unit 23 may also be disposed inside the bore.

Figure 2:
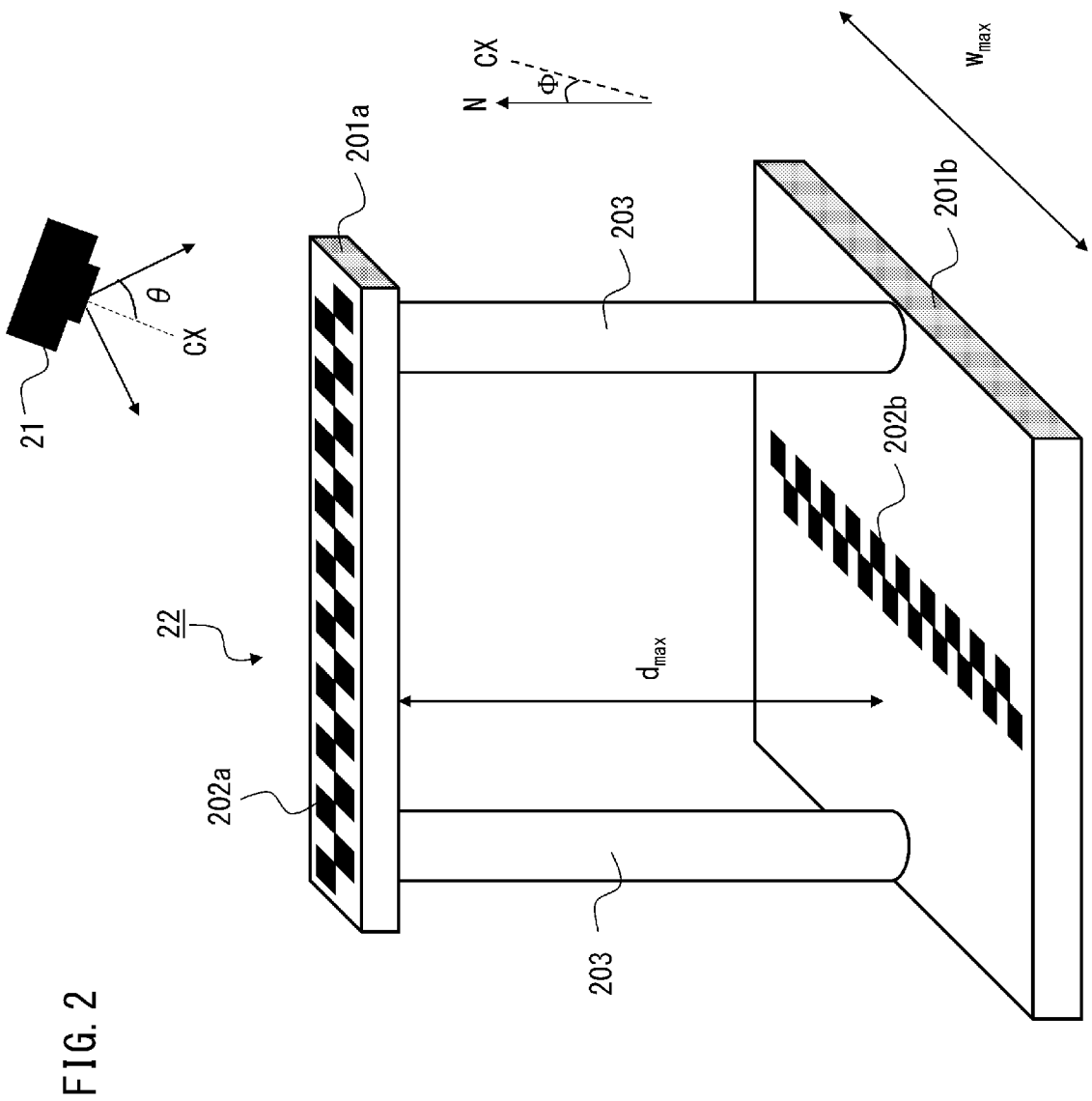
FIG. 2 is a diagram illustrating an example of a marker and patterns according to the first embodiment.
Figure 3:
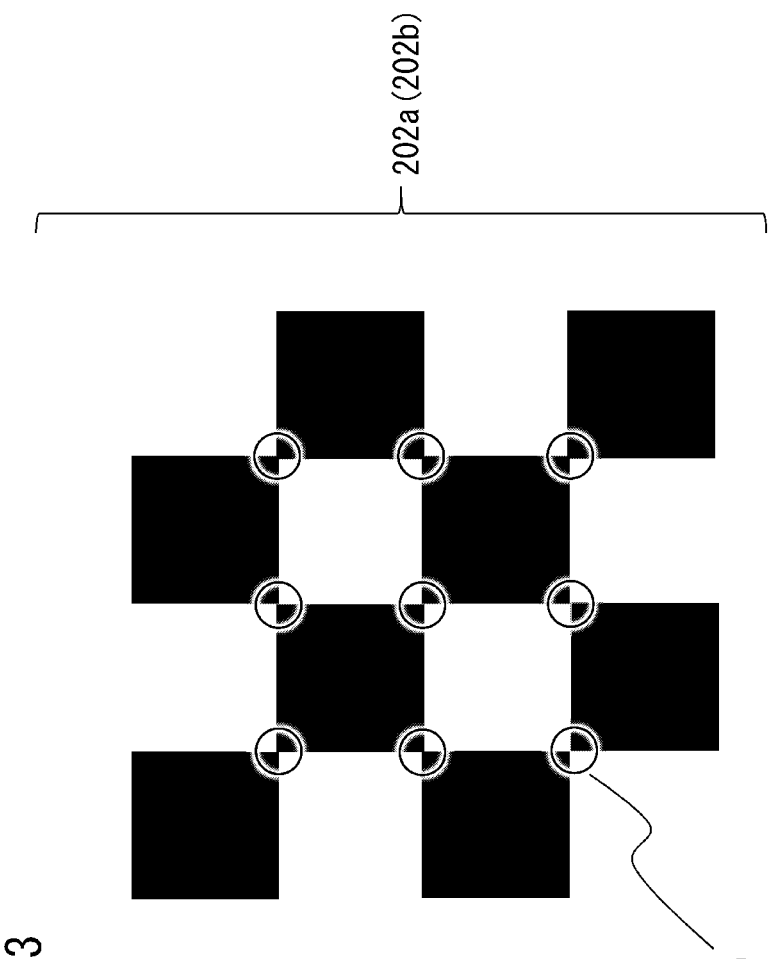
FIG. 3 is a diagram illustrating an example of the patterns according to the first embodiment.

Next, referring to FIGS. 2 to 4, a description will be given of the marker 22. In the first embodiment, the marker 22 is attached to the subject (subject to be imaged) 200, and a spatial position of the marker 22 varies with the movement of the subject 200. FIG. 2 illustrates an example of a shape of the marker 22. As illustrated in the drawing, the marker 22 has a plurality of planar structures 201a and 201b that can be detected by the movement calculation unit 23. Each of the structures 201a and 201b is typically a flat plate, but any shape can be used. To the structures 201a and 201b, patterns 202a and 202b for allowing feature points required for the calculation of the movement of the marker 22 to be calculated from a camera image are respectively added. The structures 201a and 201b mentioned herein are non-transparent flat plates and have the patterns 202a and 202b each added only to a surface on one side thereof. The marker 22 also has positioning portions 203 that connect the structures 201a and 201b to each other and position the individual structures at different positions in an imaging direction in which the subject 200 is imaged by the optical imaging unit 21. The positioning portions 203 allow a relative positional relationship between the structures 201a and the structures 201b in the imaging of the subject 200 by the optical imaging unit 21 to be held constant.

Next, referring to FIG. 3, a description will be given of the feature points of the patterns 202a and 202b. For example, when checkerboard patterns are used as the patterns 202a and 202b, respective corners (portions indicated by circles in the drawing) of white and black squares serve as feature points 29. By analyzing images of the patterns 202a and 202b captured by the optical imaging unit 21, it is possible to detect the feature points 29 from the images. Additionally, by analyzing variations with time of the feature points 29 of the patterns 202a and 202b in the captured images, it is possible to calculate the movement of the marker 22 and the movement of the subject 200 to which the marker 22 is attached.

As illustrated in FIG. 2, the feature points of the pattern 202a closer to the optical imaging unit 21 and the feature points of the pattern 202b closer to the subject 200 are disposed on two straight lines at skew positions. Accordingly, the image data generated by the optical imaging unit 21 includes the feature points present on the two straight lines at different angles (or two straight lines slightly curved due to trapezoidal distortion). These two lines can be discriminated from each other based on directions of vectors connecting coordinates of the feature points close to each other.

In general, in imaging of a marker on which patterns are three-dimensionally disposed by a camera, a moving speed of feature points of the pattern closer to the camera is higher than a moving speed of feature points of the pattern closer to a subject. As a result, these feature points are likely to be detected in a state (occlusion) where the feature points overlap each other. To avoid occurrence of the occlusion, it is necessary to increase the number of the cameras or perform heavy-load calculation for identifying the overlapping feature points. In the first embodiment, by using the marker 22 in FIG. 2, it is possible to discriminate the two straight lines described above from each other without reducing a calculation speed and reduce a possibility of occurrence of the occlusion.

The patterns 202a and 202b drawn on the structures of the marker 22 illustrated in FIG. 2 are of the same type, but any patterns may be used as long as the feature points can be calculated from the images captured by the optical imaging unit 21. In the example in FIG. 2, the example of the checkerboard patterns is illustrated, but various patterns such as circular patterns or rectangular patterns can be used. Note that, when the checkerboard patterns or the rectangular patterns are used, the corner portions of the white or black quadrilaterals in the patterns are used as the feature points, in the same manner as for the feature points 29 described above. When the circular patterns are used, gravity center portions of circles are used as the feature points. However, any method of determining the feature points may be used as long as the method allows the feature points to be accurately calculated from images of the patterns.

Figure 4:
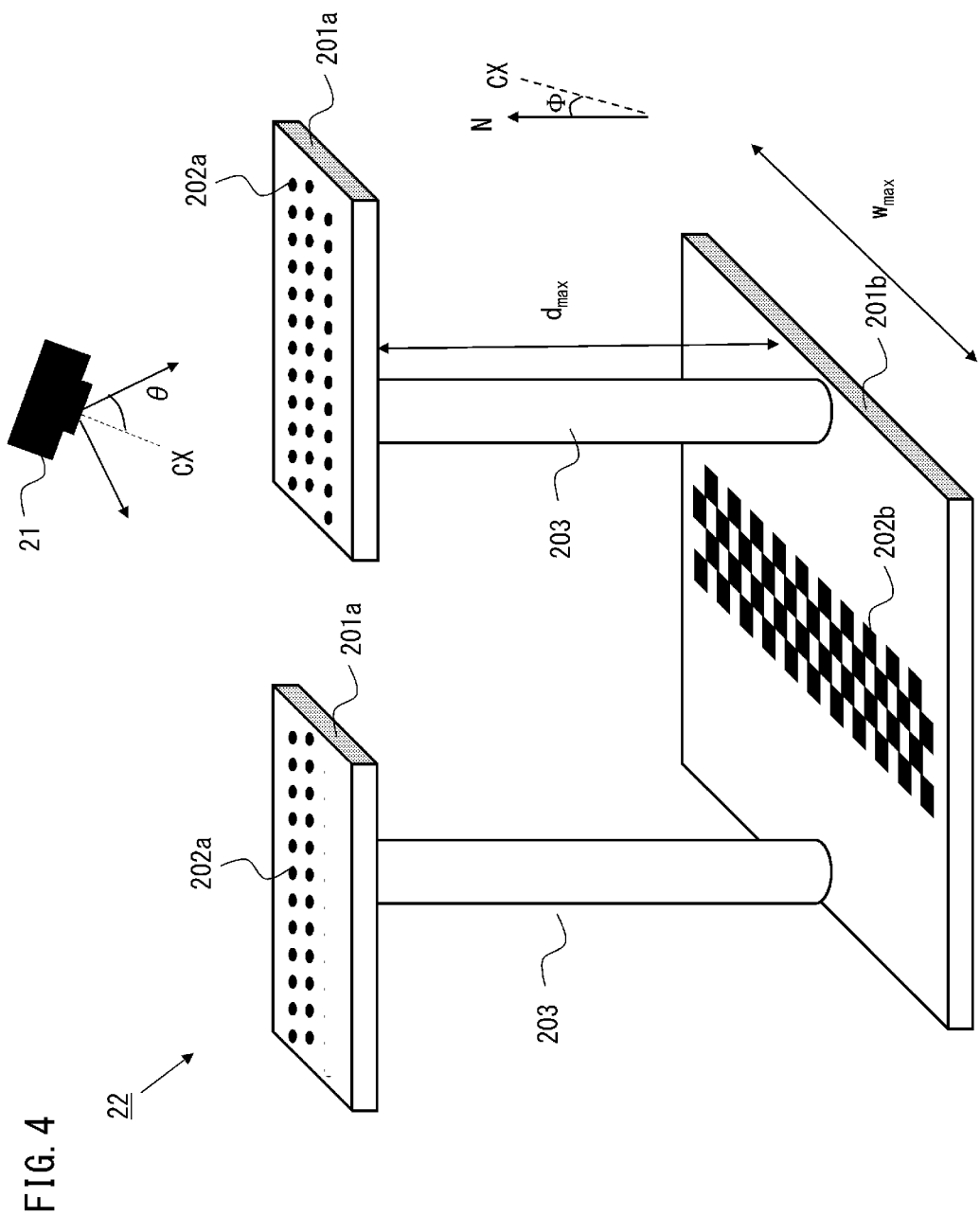
FIG. 4 is a diagram illustrating another example of the marker and the patterns according to the first embodiment.

Note that, as illustrated in FIG. 4, the numbers of the patterns to be formed on the structures or of the feature points may be different from each other. The marker 22 illustrated in FIG. 4 is different from the marker 22 illustrated in FIG. 2 in that the structure 201a is divided into two parts, and the patterns 202a are added to the respective structures 201a resulting from the division. The two structures 201a resulting from the division are connected to the structure 201b by the positioning portions 203 each having the same length. Note that the positioning portions 203 may also have different lengths. Alternatively, as illustrated in FIG. 4, it may also be possible to add the pattern 202a, including two dot lines, to one of the structures 201a and add the pattern 202a, including three dot lines, to the other structure 201a. As a result, the patterns 202a have different configurations to allow the orientation of the marker 22 or the like to be more easily specified in the captured image.

As illustrated in FIG. 4, each of the patterns 202a and the pattern 202b are different from each other depending on a distance from the optical imaging unit 21 to the subject. The patterns 202a and 202b have feature point sets each including the plurality of feature points, and the respective feature point sets of the patterns 202a and 202b are different from each other. The feature points of the patterns 202a closer to the optical imaging unit 21 and the feature points of the pattern 202b closer to the subject 200 are at skew positions. Specifically, the feature points included in the feature point sets of the patterns 202a and the feature points included in the feature point set of the pattern 202b are disposed on straight lines which are not parallel with each other. This allows the optical imaging unit 21 to extract the feature points different from each other from the patterns 202a and 202b and identify the patterns respectively formed on the individual structures in images, resulting in higher calculation accuracy of the feature points. Alternatively, the patterns 202a and the pattern 202b may also be of the same type (e.g., a checkerboard) and have different pattern symmetric properties. Even when the patterns are thus formed, it is possible to identify the patterns 202a and 202b different from each other depending on the distance from the optical imaging unit 21 to the subject.

In the example illustrated in FIGS. 2 and 4, the marker 22 in the first embodiment is characterized in that the structure 201a and the structure 201b are disposed to be spaced apart from each other by a distance not less than a predetermined distance in the imaging direction (camera imaging direction) of the optical imaging unit 21. Note that, as the distance between the structures 201a and 201b when the structures 201a and 201b are not parallel with each other, a distance specified by any measurement method such as a maximum distance between respective surfaces of the structures 201a and 201b facing each other, a minimum distance between the facing surfaces, or a distance (an average distance) between any representative points on the facing surfaces may be used appropriately. It is assumed herein that the structure 201a and the structure 201b are disposed at different positions in the imaging direction in which the subject is imaged by the optical imaging unit 21. However, the following description is also applicable to a case where the structure 201a and the structure 201b are disposed to be spaced apart from each other by a distance not less than a predetermined distance in the same plane when viewed from the optical imaging unit 21.

The camera imaging direction serving as an example of the imaging direction of the optical imaging unit 21 is defined herein. The camera imaging direction is defined as any direction in which an angle formed between an optical axis CX of the camera and a normal N to each of planes of the structures 201a and 201b on which the patterns are drawn falls within a range of satisfying the following Expression (1) with respect to an angle of view of the camera in a direction in which the camera images the subject. The angle of view of the camera is determined by the image sensor and the focal distance, which is assumed to be 20 herein.

$$\Phi < \theta \qquad (1)$$

In the case in FIG. 4, the structures 201a and 201b are flat plates and substantially parallel with each other, and therefore it is assumed that N represents a normal to each of the flat plates of the structures 201a and 201b. Note that a direction in which the normal N extends is different from a direction in which the optical axis CX of the camera extends. However, since $\Phi$ is smaller than $\theta$, the direction of the normal N to the flat plate corresponds to the imaging direction (camera imaging direction) of the optical imaging unit 21.

It is assumed herein that $d_{max}$ represents a maximum distance between the structure 201a and the structure 201b or a maximum distance between each of the structures 201a and the structure 201b in the imaging direction of the optical imaging unit 21. It is also assumed that $w_{max}$ represents a maximum length (maximum width) among lengths of the optionally selected structures 201a and 201b in a direction perpendicular to the imaging direction of the optical imaging unit 21. At this time, the following Expression (2) is preferably satisfied.

$$(\tfrac{1}{2})w_{max} < d_{max} \qquad (2)$$

This improves measurement accuracy of rotation around an axis in a direction perpendicular to the normal described later. In addition, the following Expression (3) is also preferably satisfied.

$$d_{max} < w_{max} \qquad (3)$$

Expression (3) is irrelevant to the measurement accuracy, but serves as a reference based on which a size of the entire marker 22, i.e., a size of a minimum cube including the marker 22 is limited.

Based on the above, an example of a specific size of the marker 22 is such that, when the subject 200 is assumed to be a human being and consideration is given to attachment of the marker 22 to the human being, a maximum size ($w_{max}$) of one of sides in a direction perpendicular to the camera imaging direction is preferably not more than 30 mm, and more preferably not more than 15 mm. When movement of a head region is to be measured, to prevent the marker 22 from interfering with the head RF coil, the size of the marker 22 in the camera imaging direction is preferably set to be from 7.5 mm to 30 mm.

Next, referring to FIGS. 5A to 5D, a description will be given of effects obtained when the marker 22 described above is used with reference also to a conventional example. FIGS. 5A to 5D illustrate an example using a conventional marker, in which a pattern 1202 for calculation of the feature points are added onto a flat plate serving as a structure 1201. The structure 1201 corresponds to the structure 201a or the structure 201b described above, while the pattern 1202 corresponds to the pattern 202a or 202b described above. A comparison is to be made between a change in the pattern on a camera image when the structure 1201 rotates around an axis perpendicular to the camera imaging direction (direction in which the camera optical axis extends) (FIGS. 5A and 5C) and a change in the pattern on a camera image when the structure 1201 translationally moves in a direction in which the axis perpendicular to the camera imaging direction extends (FIGS. 5B and 5D). Note that, in FIGS. 5A to 5D, movement of the marker 1202 on the camera image is schematically illustrated in each of rectangles.

In the case of an example illustrated in FIGS. 5A and 5B, on the camera images, it is substantially impossible to distinguish between the change in the pattern 1202 drawn on the flat plate when the structure 1201 rotates and the change in the pattern 1202 drawn on the flat plate when the structure 1201 translationally moves. In other words, in the method using the conventional marker, it is difficult to distinguish between the rotation of the structure 1201 and the translation of the structure 1201 described above by using camera images, and therefore an improvement in measurement accuracy cannot be expected.

Meanwhile, in the example in FIGS. 5C and 5D, the size of the flat plate is larger than in the example in FIGS. 5A and 5B, and a region where the pattern 1202 is drawn is also larger in size. In the example in FIG. 5C, the change in the pattern of the structure 1201 on the camera image in the same rotation as in FIG. 5A is larger than that in the example in FIG. 5A. Accordingly, by increasing the size of the marker in an axial direction perpendicular to the camera imaging direction, it is easier to distinguish between the rotation and the translation of the structure 1201 in the example in FIGS. 5C and 5D than in the example in FIGS. 5A and 5B. In other words, it can be said that the measurement accuracy of the movement is further improved in the example in FIGS. 5C and 5D than in the example in FIGS. 5A and 5B. However, when the size of the marker is increased in the axial direction perpendicular to the camera imaging direction, it is expected that the size of the structure 1201 is also increased to increase a load placed on the subject.

Next, referring to FIGS. 6A and 6B, a description will be given of an example using the marker 22 in the first embodiment. It is assumed that the size of the marker 22 in the axial direction perpendicular to the camera imaging direction is the same as that of the marker in FIGS. 5A to 5D. However, in the marker 22, the plurality of structures 201a and 201b are disposed to be spaced apart from each other in the camera imaging direction. The marker 22 having these structures 201a and 201b rotates in the same manner as in the example in FIGS. 5A and 5C. At this time, on the camera image, a displacement difference observed between the pattern 202a on the structure 201a more distant from a center of the rotation and the pattern 202b on the structure 201b closer to the center of the rotation is larger than in the conventional example. Meanwhile, when the marker 22 translationally moves, displacements of the pattern 202a and the pattern 202b on the camera image are the same irrespective of distances from the rotation axis to the individual structures 201a and 201b.

By thus using the markers 22, a large difference is observed between the displacement difference between the patterns when the structure rotates and the displacement difference between the patterns when the structure translationally moves. Therefore, it can be said that image analysis allows movements of the markers 22 to be more accurately distinguished from each other. In other words, it is possible to enhance the measurement accuracy of the movement of each of the markers without enlarging the size of the marker in a direction substantially perpendicular to the camera imaging direction.

Next, a description will be given of an operation of the magnetic resonance imaging apparatus 100 configured as described above. FIG. 7 is a flow chart illustrating processing to be performed mainly in association with the movement measurement system 300 when the subject 200 is to be image-captured in the magnetic resonance imaging apparatus 100.

In Step S1, an operator attaches the marker 22 to the subject 200. For example, when a head region is to be imaged, only movement of the head region is measured, and accordingly the marker 22 is fixed preferably to the subject 200 so as not to move with movement of skin. For instance, in the example in FIG. 8A, the marker 22 is added to a marker fixing device 51 which is an attachment to be attached to the head region of the subject 200, such as eyeglasses or goggles. The marker fixing device 51 is less susceptible to the movement of the skin. Then, the marker 22 is attached together with the marker fixing device 51 to the subject 200.

Note that, as long as the marker 22 follows movement to be measured, any method may be used to attach the marker 22 to the subject 200. As an attachment method, not only a method using the marker fixing device 51, but also, e.g., a method which sticks the marker directly to a body site less susceptible to the movement of the skin, such as a forehead or a nose, may be used.

Figure 8B:
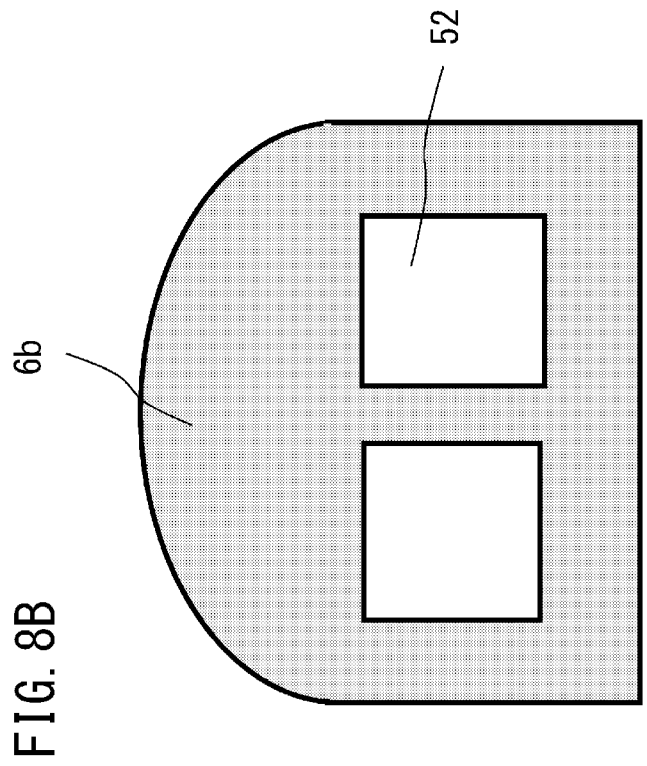
FIGS. 8A and 8B are diagrams illustrating an example of application of the marker according to the first embodiment.
Figure 8A:
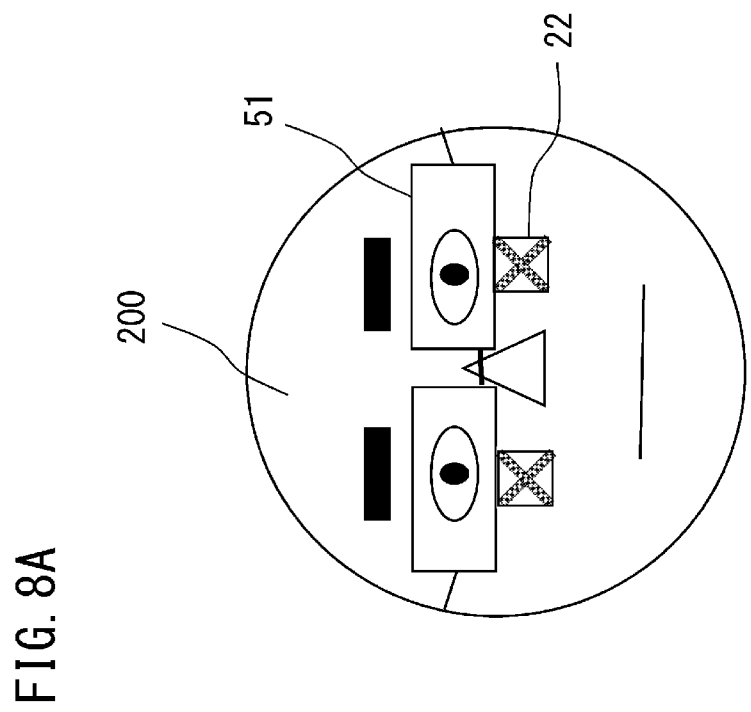

As in the example illustrated in FIG. 8B, when the head region is to be measured, a case where the subject 200 is imaged by using the RF coil 6b for testing a head region is also assumed. Consequently, the marker 22 is imaged by the optical imaging unit 21 through openings 52 of the head RF coil 6b. Accordingly, when the size of each of the openings 52 is small, it is required to be able to image the patterns 202a and 202b of the marker 22 as a whole through the openings 52. Therefore, the size of the marker 22 is preferably such that a length of each one of sides of the marker 22 in a direction substantially perpendicular to the camera imaging direction is not more than 30 mm, though depending on the size of each of the openings 52.

From a viewpoint of a load placed on the subject 200, the length of each one of the sides of the marker 22 is preferably not more than 15 mm. To prevent the marker 22 from interfering with the head RF coil, a length of the marker 22 in the camera imaging direction is preferably from 7.5 mm to 30 mm. Accordingly, the image range of the optical imaging unit 21 measures 30 mm×30 mm or more.

Meanwhile, when the head RF coil or the like is not used, i.e., when there is no limit to the size of the marker 22, the size of the marker 22 can be set so as to minimize the load placed on the subject 200. In such a case, the imaging range of the optical imaging unit 21 is also changed based on the size of the marker 22.

In Step S2, the optical imaging unit 21 of the movement measurement system 300 records a video (a set of captured images at individual times) of the marker 22 attached to the subject 200. The images captured at the individual times are transferred to the movement calculation unit 23. Note that, to prevent noise contamination, the cable used to transfer the images is preferably an optical cable or the like. As described above, in the case of the head region, the head region is imaged through the openings 52 of the head RF coil 6b. A frame rate of the imaging is normally 20 frames/second or more, and preferably 50 frames/second or more, though depending on an imaging sequence. A pixel size of each of the images is 640×480 pixels or 1024×960 pixels, but any pixel size may be used appropriately as long as a transfer speed is not affected thereby.

In Step S3, the movement calculation unit 23 calculates the movement of the marker 22 from individual frame images in the video obtained through imaging. It is assumed that an internal matrix A (3×3 rows and columns) representing internal parameters of the camera has been acquired in advance by calibration.

A specific description will be given of a method of calculating the movement of the marker 22 in the images. From the patterns 202a and 202b of the marker 22 in the camera images at the individual times, pixel positions $(u_i, v_i)$ of the feature points are calculated. Note that i is an index added to each of the pixel positions when there are the plurality of pixel positions, and may also be omitted depending on occasions. When the patterns 202a and 202b are checkerboard patterns, the respective corner portions of white and black rectangles are assumed to be the feature points. Relative positional relationships between the individual feature points of the patterns 202a and 202b of the marker 22 are already known, and three-dimensional coordinates of each of the feature points in a coordinate system of the marker 22 are given by $(m_{xi}, m_{yi}, m_{zi})$. Note that the pixel position $(u_i, v_i)$ in a camera coordinate system of the optical imaging unit 21 and the coordinates $(m_{xi}, m_{yi}, m_{zi})$ of the corresponding feature point in the marker coordinate system can be represented by the following Expression (4).

$$\begin{bmatrix} u \\ v \\ 1 \end{bmatrix} = AP \begin{bmatrix} m_x \\ m_y \\ m_z \\ 1 \end{bmatrix} \quad (4)$$

In the Expression (4), A represents the internal matrix (3×3 rows and columns) of the camera, while P represents a projection matrix (3×4 rows and columns) including a rotation matrix and a translation matrix. Note that P is represented by the following Expression (5).

$$P = \begin{bmatrix} R_{11} & R_{12} & R_{13} & t_x \\ R_{21} & R_{22} & R_{23} & t_y \\ R_{31} & R_{32} & R_{33} & t_z \end{bmatrix} = \begin{bmatrix} R_{11} & R_{12} & R_{13} \\ R_{21} & R_{22} & R_{23} \\ R_{31} & R_{32} & R_{33} \end{bmatrix} + \begin{bmatrix} t_x \\ t_y \\ t_z \end{bmatrix} = R + t \quad (5)$$

In the Expression (5), R and t are respectively represented by the following Expressions (6) and (7).

$$R = \begin{bmatrix} R_{11} & R_{12} & R_{13} \\ R_{21} & R_{22} & R_{23} \\ R_{31} & R_{32} & R_{33} \end{bmatrix} = \begin{bmatrix} \cos\beta\cos\gamma & -\cos\beta\sin\gamma & \sin\beta \\ \sin\alpha\sin\beta\cos\gamma + \cos\alpha\sin\gamma & -\sin\alpha\sin\beta\sin\gamma + \cos\alpha\cos\gamma & -\sin\alpha\cos\beta \\ -\cos\alpha\sin\beta\cos\gamma + \sin\alpha\sin\gamma & \cos\alpha\sin\beta\sin\gamma + \sin\alpha\cos\gamma & \cos\alpha\cos\gamma \end{bmatrix} \quad (6)$$

$$t = \begin{bmatrix} t_x \\ t_y \\ t_z \end{bmatrix} \quad (7)$$

In the Expressions (6) and (7), $\alpha$, $\beta$, and $\gamma$ represent rotation angles around the x-, y-, and z-axes which represent three degrees of rotational freedom, while $t_x$, $t_y$, and $t_z$ represent amounts of movement in x-, y-, and z-directions which represent three degrees of translational freedom. These variables allow the movement of the marker 22 in the images to be represented.

The projection matrix P represents, for the corresponding feature point, a transformation matrix from the marker coordinate system to the camera coordinate system. P has twelve variables (having a six degrees of freedom). Accordingly, the three-dimensional coordinates of at least three feature points in the marker coordinate system are already known and, when camera pixels corresponding thereto are known, P can be calculated based on the foregoing Expression (5).

For example, it is assumed that $P_{t0}$ represents the projection matrix obtained from a camera image acquired at a given time $t_0$, and $P_{t1}$ represents the projection matrix obtained from a camera image acquired at a next frame time $t_1$. At this time, movement $(P_{camera, t0 \to t1})$ of the marker 22 between the times $t_0$ and $t_1$ is represented by the following Expression (8).

$$P_{camera, t0 \to t1} = P_{t1} P^{-1}_{t0} \quad (8)$$

Thus, it is possible to calculate movement of the marker 22 at six degrees of freedom $(\alpha, \beta, \gamma, t_x, t_y, t_z)$. Note that the calculation method described herein is a mere example, and another calculation method may also be used as long as the method allows six-degree-of-freedom movement of the marker 22 at each of the times to be calculated. Also, a case where the movement of the marker 22 is calculated from the images obtained through imaging by the one camera is assumed herein, but the movement of the marker 22 may also be calculated using the foregoing Expressions from images obtained through imaging by two or more cameras. When relative positions of the feature points of the marker 22 are unknown, a stereo camera may also be used to obtain the three-dimensional coordinates of each of the feature points. In this case, the three-dimensional coordinates $(m_{xi}, m_{yi}, m_{zi})$ of each of the feature points correspond to three-dimensional coordinates calculated using the stereo camera.

In Step S4, the movement calculation unit 23 transforms the six-degree-of-freedom movement $(P_{camera, t0 \to t1})$ of the marker 22 in the camera coordinate system calculated at each of the times to an MRI apparatus coordinate system. Note that the MRI apparatus coordinate system is a coordinate system specific to the MRI apparatus. When there is no change in a relationship between a position at which the camera is disposed and a position of the MRI apparatus, a transformation matrix $P_{camera \to MRI}$ from the camera coordinate system to the MRI apparatus coordinate system can be obtained in advance. For example, by causing the MRI apparatus and the camera to image a phantom having the same feature points or a plurality of feature points having a known positional relationship therebetween, it is possible to calculate the movement of the marker 22 through the same calculation as described in Step S3. Note that, as long as the transformation matrix $P_{camera \to MRI}$ from the camera coordinate system to the MRI apparatus coordinate system can be calculated, another calculation method may also be used. When $P_{camera \to MRI}$ has been calculated in advance, the movement ($P_{MRI, t0 \to t1}$) of the marker (subject) in the MRI apparatus coordinate system can be calculated based on the following Expression (9).

$$P_{MRI, t0 \to t1} = P_{camera, t0 \to t1} P_{camera \to MRI} \quad (9)$$

In Step S5, the movement calculation unit 23 transmits the movement ($P_{MRI, t0 \to t1}$) of the marker 22 (subject) in the MRI apparatus coordinate system which is calculated at each of the times to the magnetic field control unit 10. When a time period required for transmission of information on the movement calculated from the image captured by the camera to the magnetic field control unit is defined as a latency, the latency is not more than 50 milliseconds, and preferably not more than 20 milliseconds. This allows the calculation accuracy of the movement of the marker 22 to be further enhanced.

In Step S6, to correct the movement of the subject, the magnetic field control unit 10 corrects a gradient magnetic field and a frequency based on the movement. Next, in Step S7, the optical imaging unit 21 determines whether or not the imaging of the subject has been completed. When the imaging has not been completed (NO in S7), the processing returns to Step S2. Meanwhile, when the imaging has been completed (YES in S7), the processing advances to Step S8.

In Step S8, the MRI apparatus generates image data through image reconstruction. The data collection unit 11b collects magnetic resonance data subjected to movement correction which is output from the reception unit 9 at each of the times. The data collection unit 11b stores the collected magnetic resonance data in the storage unit 11d. Then, the reconstruction unit 11c performs post-processing, i.e., reconstruction such as Fourier transform on the magnetic resonance data stored in the storage unit 11d to generate spectrum data or MR image data of intended nuclear spin in the subject 200. As a result, even when the subject 200 moves during imaging, it is possible to hold an imaging area constant, and therefore it is possible to generate the image data in which motion artifacts are reduced.

As described above, with the magnetic resonance imaging apparatus in the first embodiment, when the marker is attached to the subject and imaging is performed, it is possible to accurately detect the movement of the marker and perform image generation. As a result, it is possible to prevent occurrence of an unneeded phenomenon such as motion artifacts due to movement of the subject in a captured image and also reduce a load resulting from imaging of the subject, such as reimaging. When the MRI apparatus is used as a modality, collecting information needed to obtain one image requires a time period longer than that needed when another modality is used. Accordingly, when the MRI apparatus is used as the modality, it is expected to obtain a particularly high effect by using the marker described above.

Other Embodiments

The embodiment described above merely shows a specific example of the present disclosure. The scope of the present disclosure is not limited to a configuration of the embodiment described above, and various embodiments within the scope that does not change the gist of the invention can be used. A description will be given below of some modifications of the embodiment described above. Note that, in each of the modifications described below, the same components as used in the embodiment described above are given the same reference numerals, and a detailed description thereof is omitted.

First Modification

Figure 9A:
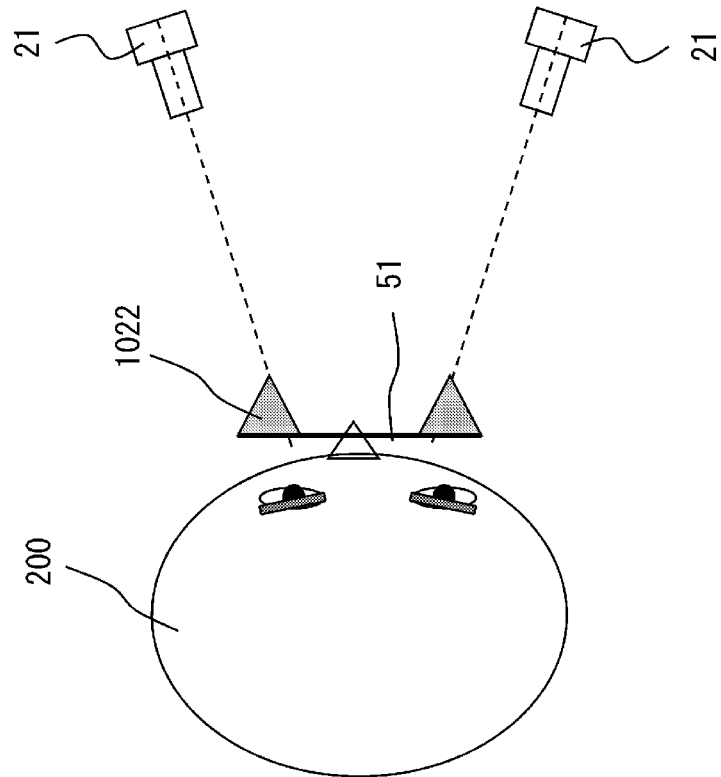
FIGS. 9A and 9B are diagrams illustrating an example of a layout of a marker and a camera according to a modification.

A description will be given of the first modification. The first modification is different from the embodiment described above in a shape of each of markers and in the number of the cameras included in the optical imaging unit. FIG. 9A illustrates a shape of each of markers 1022 in the first modification. Each of the markers 1022 has a three-dimensional shape of a polygonal pyramid and includes triangular flat plates 1201 serving as a plurality of structures. To a surface of each of the flat plates 1201, a pattern 1202 having feature points is added. Note that the marker 1022 is configured such that an angle Φ formed between a normal to the flat plate 1201 and the optical axis of the camera is smaller than an angle of view θ of the camera. As illustrated in FIG. 9A, in the first modification, the width $w_{max}$ of the marker 1022 is 15 mm and the height $d_{max}$ of the marker 1022 is 15 mm.

Figure 9B:
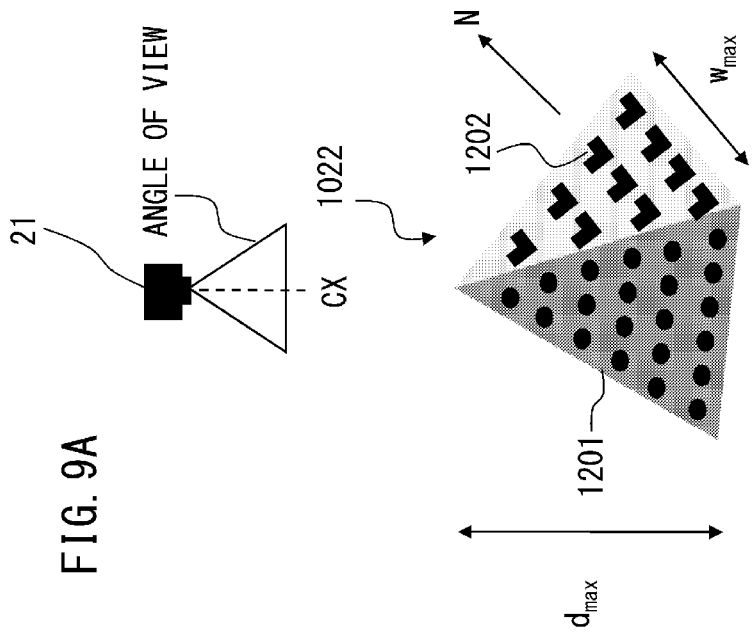

As illustrated in FIG. 9B, the two markers 1022 are attached via the marker fixing device 51 to the subject 200 to be imaged by the optical imaging unit 21. Consequently, the two markers 1022 are fixed by the marker fixing device 51 to have a constant relative positional relationship therebetween. The markers 1022 are attached to the nose of the subject 200 by the marker fixing device 51. By attaching the marker 1022 to the nose, it is possible to minimize influence exerted by movement of the markers 1022 due to the movement of the skin of the subject 200 on the detection accuracy of the movement of the markers 1022. Note that the markers 1022 may also be stuck to the forehead of the subject 200.

In addition, in the first modification, the optical imaging unit 21 has at least two cameras. In addition, an imaging range of each of the cameras is set such that the individual cameras image the different markers. FIG. 9B illustrates a case where the two cameras 21 serving as the optical imaging unit are used but, to improve the measurement accuracy of the movement of the markers 1022, it may also be possible to image one of the markers 1022 by using the two or more cameras 21. By thus configuring the cameras 21, even when the markers 1022 are small in size, as long as the relative positional relationship between the individual markers 1022 is constant and already known, the plurality of markers 1022 can be regarded as an integral marker. As a result, in the magnetic resonance imaging apparatus 100, it is possible to further improve the measurement accuracy of the movement of the markers.

Second Modification

Next, a description will be given of the second modification. The second modification is different from the first embodiment described above in the configuration of the optical imaging unit. The second modification assumes measurement of the movement of the head region of the subject 200. As illustrated in FIG. 10, the camera 21 that images the subject 200 is fixed to the top plate 41. The camera 21 uses a reflective plate 71 such as a mirror to image the marker 22 fixed to the subject 200 through the openings of the head RF coil 6b. The reflective plate 71 changes the camera imaging direction (direction of the optical axis of the camera 21) with respect to the subject 200. The reflective plate 71 is formed of a non-magnetic material, and can be formed of any raw material as long as the raw material can optically reflect the subject 200. Examples of the reflective plate 71 include a mirror obtained by performing aluminum deposition processing on acryl, a half mirror having a dielectric film attached thereto, and the like. The reflective plate 71 is rotatively provided on a support arm 73 such that an angle of the reflective plate 71 can manually be adjusted.

In such a configuration, the camera 21 need not be disposed in the viewing field of the subject 200, and therefore it is possible to ensure a wide viewing field for the subject 200 and expect an effect of reducing an oppressive feeling given by each of the internal units of the apparatus 100 to the subject 200 during the imaging. In addition, the camera 21 and the reflective plate 71 are integrated with each other by a support unit 72 and the support arm 73, and the support unit 72 can be moved over the top plate 41 of the bed. In other words, in the second modification, the camera 21, the reflective plate 71, the support unit 72, and the support arm 73 serve as a movable optical imaging unit 2021.

The movable optical imaging unit 2021 is movable along a center axis of the bore. For example, the support unit 72 is a structure (movable carriage) that moves along a rail (not shown) provided on the top plate 41. To the support unit 72, a wheel (not shown) for enhancing traveling performance on the rail is attached. Note that, when the support unit 72 can travel on the rail, it may also be possible to form a surface in contact with the rail of a material having a low frictional coefficient with respect to the rail, instead of using the wheel. The rail is formed of a non-magnetic material which does not affect a magnetic field to be used for magnetic resonance imaging in the magnetic resonance imaging apparatus 100.

In the second modification, the optical imaging unit 2021 described above allows the position of the camera 21 to be adjusted based on the subject 200. Consequently, the camera 21 can more accurately image the marker 22 attached to the subject 200. This allows the measurement accuracy of the movement of the subject 200 to be further enhanced.

Third Modification

Next, a description will be given of the third modification. The third modification is different from the first embodiment described above in the configuration of the optical imaging unit. The third modification assumes measurement of the movement of the head region of the subject 200. As illustrated in FIG. 11, the camera 21 that images the subject 200 is disposed outside the bore. The camera may also be fixed to a device such as the top plate 41 as long as the camera is located outside the bore. FIG. 11 illustrates an example using the one camera 21 but, to improve the measurement accuracy of the movement, a plurality of the cameras are used preferably. In addition, the reflective plate 71 is used to image the marker 22 fixed to the subject 200 through the openings of the head RF coil 6b. The reflective plate 71 changes the camera imaging direction (direction of the optical axis of the camera 21) with respect to the subject 200.

In such a configuration, the camera 21 need not be disposed in the viewing field of the subject 200, and therefore it is possible to ensure a wide viewing field for the subject 200 and expect an effect of reducing an oppressive feeling given by each of the internal units of the apparatus 100 to the subject 200 during the imaging. In addition, since the camera serving as an electronic device that may cause image noise can be disposed as far as possible from the MRI apparatus, an effect of further reducing occurrence of noise in a captured image can be expected. Note that, in the same manner as in the second modification, the reflective plate 71 may also be fixed to the top plate 41 by the support unit 72 and configured to be movable.

Fourth Modification

Figure 12:
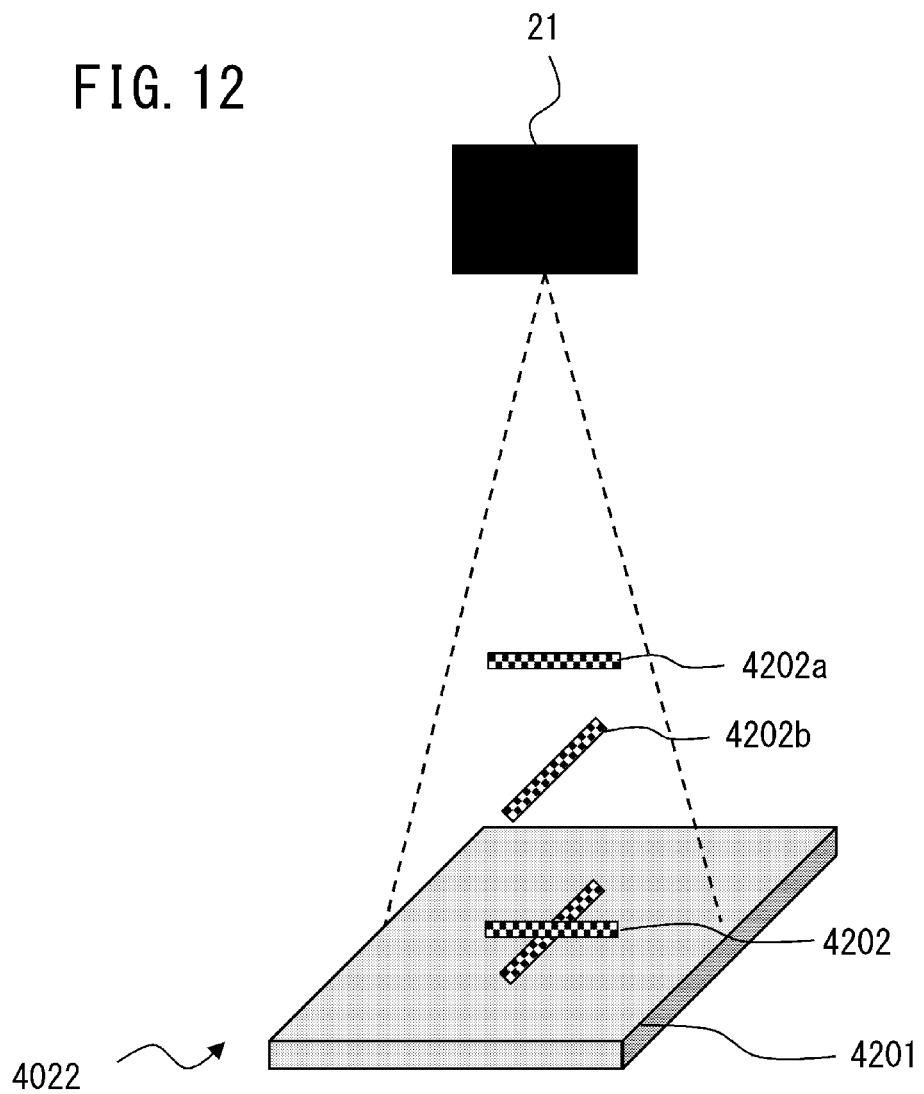
FIG. 12 is a diagram illustrating an example of application of a marker according to yet another modification.

Next, a description will be given of the fourth modification. The fourth modification is different from the first embodiment described above in a configuration of the marker. Referring to FIG. 12, a description will be given of a difference between the fourth modification and the first embodiment. As illustrated in FIG. 2, the marker 22 in the first embodiment described above includes the patterns 202a and 202b having different heights (positions) in the imaging direction of the camera 21. As a result, in the captured image, the size of the pattern 202a closer to the camera 21 is larger at least in the imaging direction of the camera 21 than when a marker including only one flat plate is used. In the captured image, the patterns of the marker 22 may be represented appropriately as patterns having different heights in the imaging direction of the camera 21.

Accordingly, as illustrated in an example in FIG. 12, as a marker 4022 in the fourth modification, a structure in which a three-dimensional pattern 4202 is recorded by hologram on a flat plate 4201 is used. Consequently, the marker 4202 is added to a plane but, in the image captured by the camera 21, three-dimensional virtual images 4202a and 4202b are reproduced. As a result, in the captured image, patterns having different heights in the imaging direction of the camera 21 are observe and, in the imaging direction in which the subject 200 is imaged by the optical imaging unit 21, the structures are reproduced at positions at different distances from the camera 21. By particularly using Lippman hologram as the hologram to be used for the pattern 4202, it is possible to reproduce higher-accuracy spatial structures or patterns in the image.

Therefore, according to the fourth modification, it is possible to enhance the measurement accuracy of the movement of the marker in the same manner as when the marker is three-dimensionally formed as described above, while reducing the size of the marker in the imaging direction of the camera and thereby preventing interference between the marker and each of the internal units of the apparatus.

The technique according to the present disclosure allows the movement of the marker to be used when the subject is imaged to be accurately detected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-109120, filed on Jun. 24, 2020, which is hereby incorporated by reference herein in its entirety.

What is claimed is:

1. A medical image diagnostic apparatus comprising:
at least one imaging unit;
a detection unit;
at least one memory storing instructions; and
at least one processor that is configured, upon execution of the stored instructions, to provide instructions to the at least one imaging unit and the detection unit, wherein:
the at least one imaging unit is configured to capture images of a subject and a marker placed on the subject; and
the detection unit is configured to detect movement of the marker from the images captured by the imaging unit, wherein the marker includes a plurality of planar structures that can be detected by the detection unit, and wherein the planar structures are provided with different patterns according to distances to the subject and are spaced apart from each other with a distance no less than a predetermined distance.

2. The medical image diagnostic apparatus according to claim 1, wherein the planar structures are connected to each other and disposed at different positions in an imaging direction in which the images of the subject are captured by the imaging unit.

3. The medical image diagnostic apparatus according to claim 1, wherein each of the plurality of planar structures is provided with a pattern having a feature point that allows the detection unit to detect the movement of the marker.

4. The medical image diagnostic apparatus according to claim 3, wherein the pattern having the feature point includes a plurality of patterns for extracting a plurality of feature point sets based on distances to the subject, wherein the feature points included in the feature point set are on different straight lines corresponding to the individual feature point sets, and wherein the different straight lines corresponding to the individual feature point sets are not parallel with each other.

5. The medical image diagnostic apparatus according to claim 4, wherein at least two patterns of the plurality of patterns for extracting the plurality of feature point sets are the same type of patterns.

6. The medical image diagnostic apparatus according to claim 3, wherein the pattern is provided on only one of surfaces of the planar structure.

7. The medical image diagnostic apparatus according to claim 1, wherein the marker has a size which allows a cross-sectional area of a virtual cube including the marker to fall within an imaging range of the imaging unit.

8. The medical image diagnostic apparatus according to claim 1, wherein the imaging unit is an optical camera.

9. The medical image diagnostic apparatus according to claim 1, wherein the marker is added to an attachment that is attached to a head region of the subject.

10. The medical image diagnostic apparatus according to claim 9, wherein the images of the marker are captured by the imaging unit through an opening of the attachment.

11. A marker for detecting movement of a subject, comprising:

a plurality of planar structures that can be detected by a medical image diagnostic apparatus, wherein the marker is placed on the subject and images of the marker are captured together with the subject by the medical image diagnostic apparatus so as to reduce a motion artifact in the images captured by the medical image diagnostic apparatus, and wherein the planar structures are provided with different patterns according to distances to the subject and are spaced apart from each other by a distance not less than a predetermined distance.

* * * * *